(12) United States Patent
Mishima

(10) Patent No.: US 6,638,260 B2
(45) Date of Patent: Oct. 28, 2003

(54) DISPOSABLE DIAPER

(75) Inventor: Yoshitaka Mishima, Kagawa-ken (JP)

(73) Assignee: Uni-Charm Corp., Ehime-ken (JP)

( * ) Notice: Subject to any disclaimer, the term of this patent is extended or adjusted under 35 U.S.C. 154(b) by 0 days.

(21) Appl. No.: 10/025,658

(22) Filed: Dec. 19, 2001

(65) Prior Publication Data

US 2002/0077615 A1 Jun. 20, 2002

(30) Foreign Application Priority Data

Dec. 19, 2000 (JP) ........................................ 2000-385698

(51) Int. Cl.$^7$ ................................................ A61F 13/15
(52) U.S. Cl. ............................ 604/385.01; 604/385.201
(58) Field of Search ...................... 604/385.01, 385.28, 604/385.26, 385.16, 385.201, 385.29

(56) References Cited

U.S. PATENT DOCUMENTS

| | | | |
|---|---|---|---|
| 3,650,273 A | 3/1972 | Scharr | |
| 3,776,233 A | 12/1973 | Scharr | |
| 3,848,599 A | 11/1974 | Scharr | |
| 3,885,568 A | 5/1975 | Scharr | |
| 3,943,930 A | 3/1976 | Schaar | |
| 4,500,316 A | 2/1985 | Damico | |
| 4,573,990 A | 3/1986 | Ohsaki | |
| 5,407,438 A | * 4/1995 | Hedlund et al. | 604/385.26 |
| 5,558,660 A | * 9/1996 | Dreier | 604/385.19 |
| 5,746,732 A | * 5/1998 | Olsson et al. | 604/385.28 |
| 6,102,892 A | * 8/2000 | Putzer et al. | 604/385.01 |
| 6,120,486 A | * 9/2000 | Toyoda et al. | 604/385.29 |
| 6,132,410 A | * 10/2000 | Van Gompel et al. | 604/385.25 |
| 6,152,907 A | * 11/2000 | Widlund et al. | 604/385.08 |

FOREIGN PATENT DOCUMENTS

| | | |
|---|---|---|
| JP | 10-24060 | 1/1998 |
| JP | 10-24066 | 1/1998 |
| JP | 10-43234 | 2/1998 |

\* cited by examiner

*Primary Examiner*—Weilun Lo
*Assistant Examiner*—Jacqueline F Stephens
(74) *Attorney, Agent, or Firm*—Butzel Long

(57) ABSTRACT

A disposable diaper that includes a base sheet and an absorbent panel placed onto the base sheet and provided with pleats defined by folding the base sheet together with the panel in a transverse direction across a crotch regions front zone adjacent to a front waist region and a crotch region's rear zone adjacent to a rear waist region, respectively. Transversely opposite end regions of the respective pleats are joined to side flaps, respectively.

6 Claims, 6 Drawing Sheets

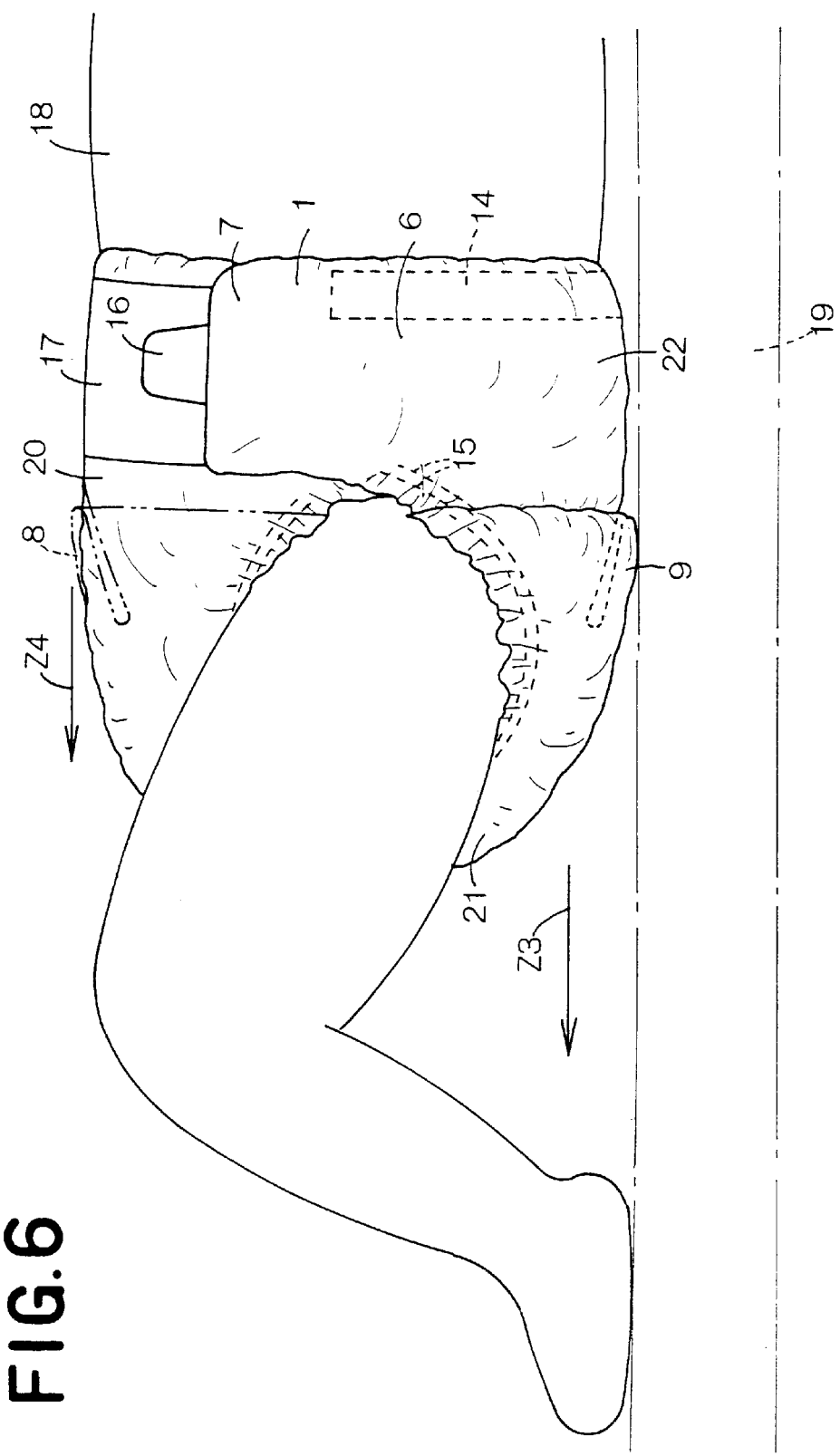

DISPOSABLE DIAPER

BACKGROUND OF THE INVENTION

This invention relates to a disposable diaper for absorption and containment of body wastes.

Conventional open-type disposable diapers basically comprise a liquid-pervious topsheet, a liquid-impervious base sheet and a liquid-absorbent panel so as to configure, in a longitudinal direction, a front waist region, a rear waist region and a crotch region extending between these waist regions. Some of the diapers further comprise a pair of end flaps extending in a transverse direction immediately outside longitudinal opposite ends of the panel and a pair of side flaps extending in the longitudinal direction immediately outside transversely opposite side edges of the panel.

To wear the diaper, the side flaps in the rear waist region may be placed upon the outer side of the side flaps in the front waist region, then the respective tape fasteners may be anchored on the target tape strip to connect the front and rear waist regions with each other. Upon connection of the front and rear waist regions, a waist-hole and a pair of leg-holes are defined in the diaper. Such diaper is disclosed, for example, in Japanese Patent Application Publication Nos. 1998-24066A; 1998-24060A. and 1998-43234A.

In the conventional diaper as has been described above, body wastes must be immediately absorbed by the liquid-absorbent panel and contained therein in order to prevent the body wastes from leaking from the diaper. To this end, the inner surface of the diaper must be kept in contact with the wearer's skin during use of the diaper. Here is an anxiety for such diaper that one of the front and rear waist regions of the diaper might slip down along the wearer's waist as the wearer lying on the bedding moves in the longitudinal direction due to a frictional force generated between the diaper and the bedding. Should the front or rear waist region slip down, the inner surface of the diaper will be spaced apart from the wearer's skin and it will be difficult for the panel to absorb the body wastes and prevent leakage thereof.

It is an object of this invention to provide a disposable diaper free from anxiety that the front waist region and/or the rear waist region might slip down along the wearer's torso during use of the diaper and adapted to reliably absorb and contain body wastes in the liquid-absorbent panel.

According to this invention, there is provided a disposable diaper having a front waist region, a rear waist region and a crotch region extending therebetween comprising a substantially liquid-impervious base sheet, a liquid-absorbent panel placed onto the base sheet, a pair of end flaps extending in a transverse direction immediately outside longitudinal opposite ends of the panel and a pair of side flaps extending in a longitudinal direction immediately outside transversely opposite side edges of the panel.

The diaper further comprises at least one pleat defined by folding the base sheet and the panel together, the last least one pleat extending in the transverse direction across at least one of a front zone of the crotch region adjacent to the front waist region and a rear zone of the crotch region adjacent to the rear waist region so that the pleat has transversely opposite end regions thereof joined to the side flaps, respectively.

According to one embodiment of this invention, the pleat extends outward from an outer surface of the base sheet and is normally collapsed onto the end flaps.

BRIEF DESCRIPTION OF THE DRAWINGS

FIG. 6 is another side view of the diaper as being worn with its front and rear waist regions connected to each other.

BRIEF DESCRIPTION OF THE PREFERRED EMBODIMENTS

Details of a disposable diaper according to this invention will be more fully understood from the description of an open-type diaper given hereunder with reference to the accompanying drawings as one embodiment of this invention.

Figure 1:
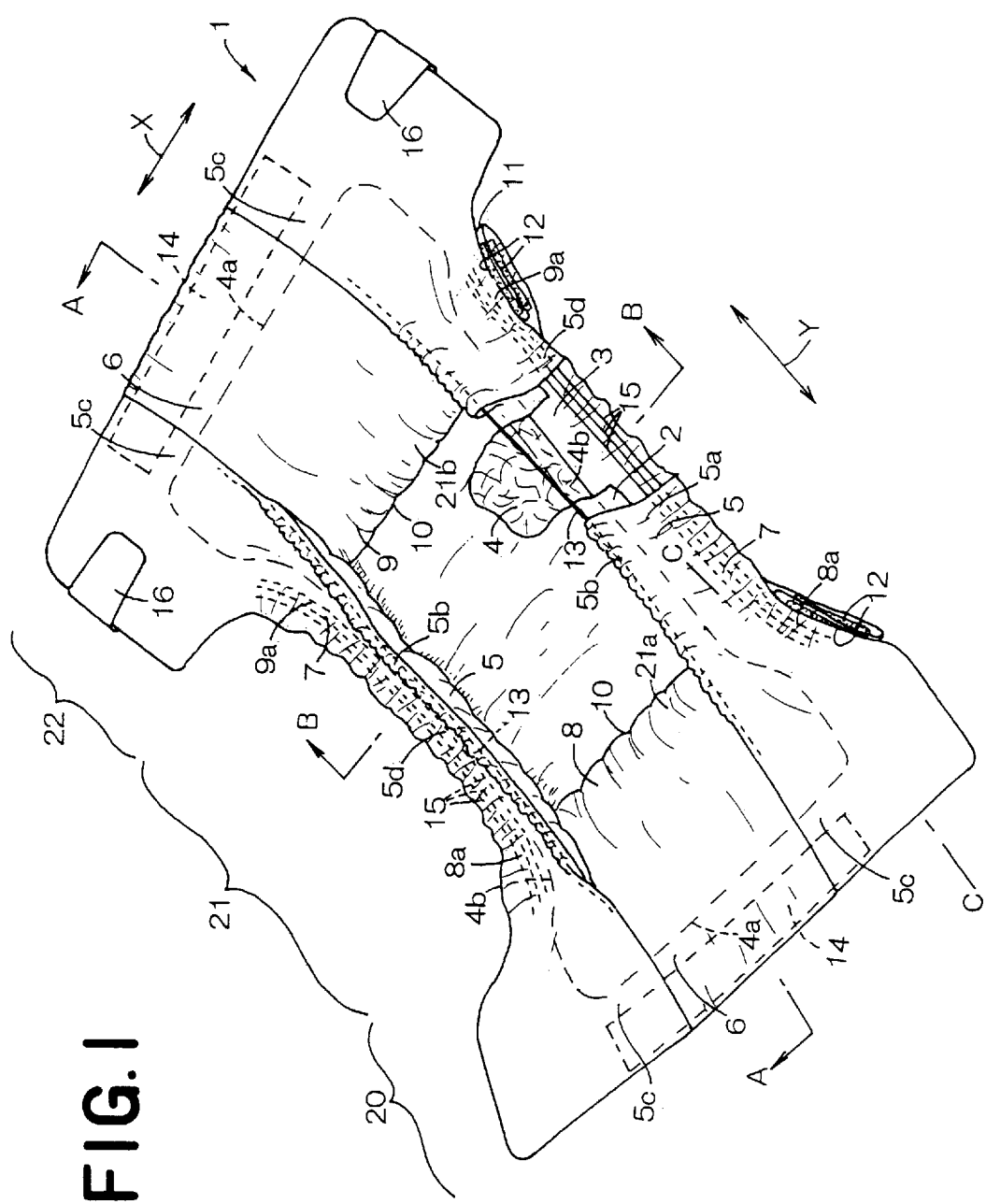
FIG. 1 is a partially cutaway perspective view showing a diaper viewed from the side of the topsheet.
Figure 2:
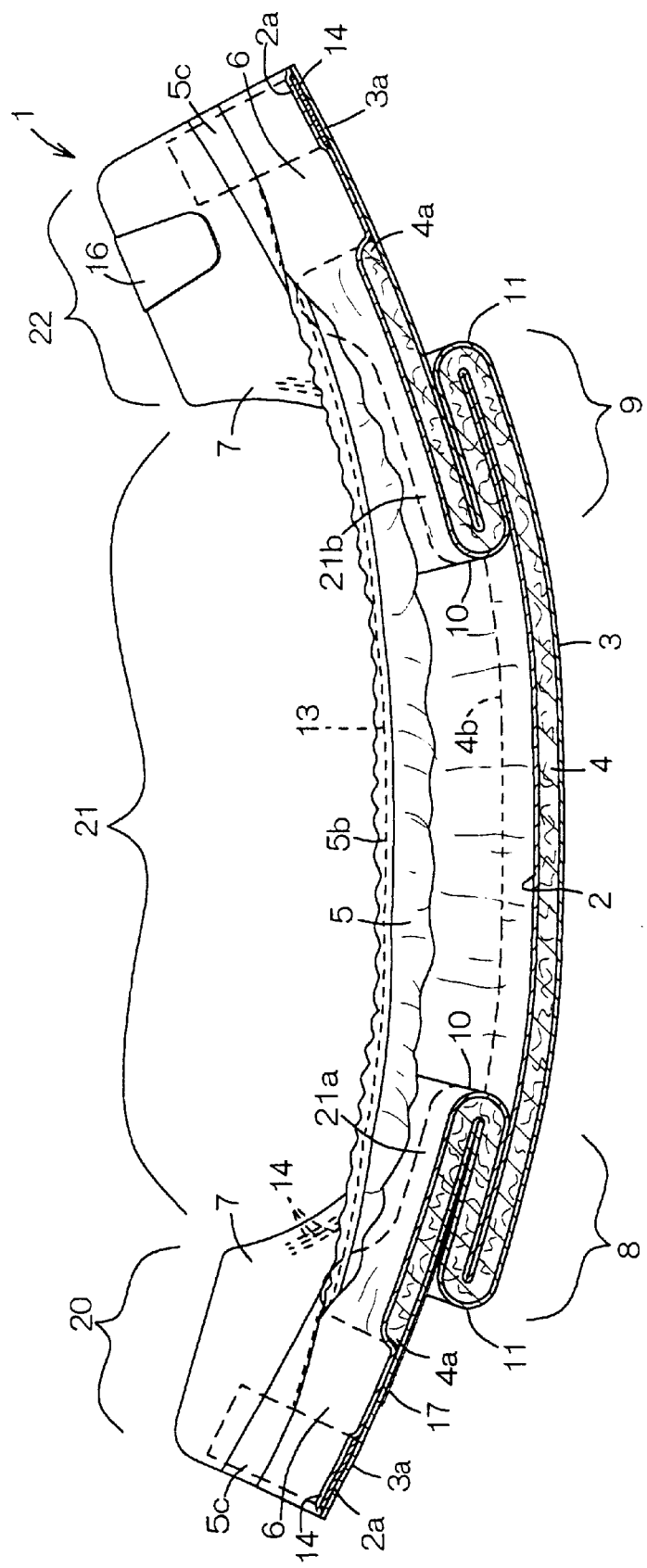
FIG. 2 is a cross-sectional view taken along a line A—A in FIG. 1.
Figure 3:
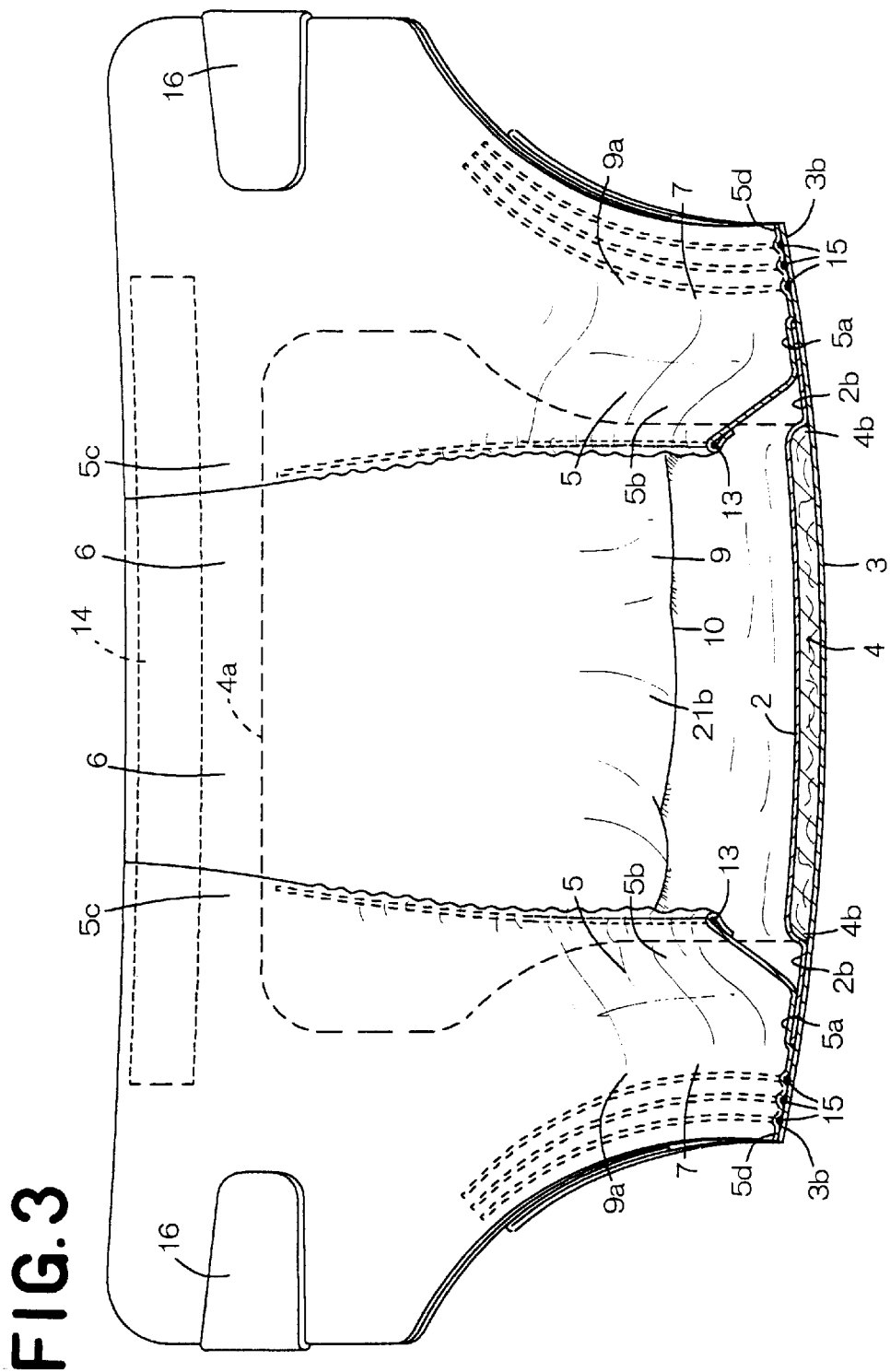
FIG. 3 is a cross-sectional view taken along a line B—B in FIG. 1.
Figure 4:
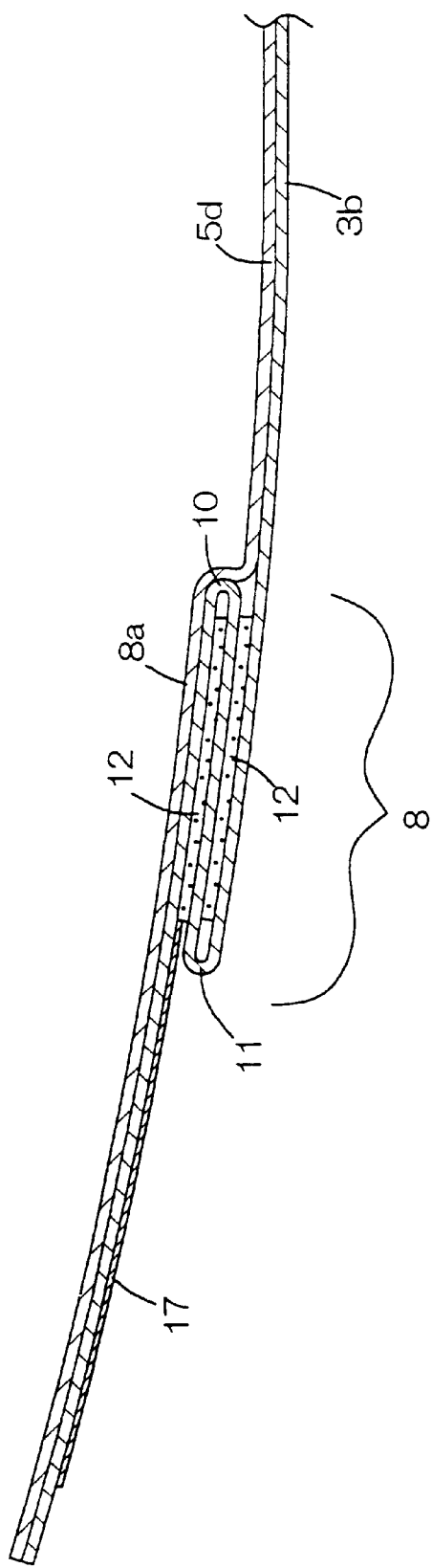
FIG. 4 is a cross-sectional view taken along a line C—C in FIG. 5.

FIG. 1 is a partially cutaway perspective view showing a diaper viewed from the side of the topsheet, FIG. 2 is a sectional view taken along a line A—A in FIG. 1, FIG. 3 is a cross-sectional view taken along a line B—B in FIG. 1 and FIG. 4 is a cross-sectional view taken along a line C—C in FIG. 1. In FIG. 1, a transverse direction is indicated by an arrow X and a longitudinal direction is indicated by an arrow Y. Expression used herein "inner surfaces of a topsheet 2 and base sheet 3" should be understood to be those of these sheets 2, 3 which face a panel 4 and expression used herein "outer surfaces of these sheets 2, 3" should be understood to be those which do not face the panel 4.

The diaper 1 basically comprises the liquid-pervious topsheet 2, the substantially liquid-impervious base sheet 3 and the liquid-absorbent panel 4 disposed between these sheets 2, 3. In addition to these components, the diaper 1 includes a pair of substantially liquid-impervious leak-barrier cuffs 5.

The diaper 1 is composed, in the longitudinal direction, of a front waist region 20, a rear waist region 22 and a crotch region 21 extending between these waist regions 20, 22. The diaper 1 has a pair of end flaps 6 extending in the transverse direction outside transversely opposite ends 4a of the panel 4 and a pair of side flaps 7 extending in the longitudinal direction outside transversely opposite side edges of the panel 4 so that; in the crotch region 21, these side flaps 7 are convexly formed inward transversely of the diaper 1 in generally arc shape.

The diaper 1 is formed with a pleat 8 extending in the transverse direction across the crotch region's front zone 21a adjacent the front waist region 20 and with a pleat 9 extending in the transverse direction across the crotch region's rear zone 21b adjacent the rear waist region 22.

These pleats 8, 9 are defined by folding the topsheet 2, the base sheet 3 and the panel 4 together. In each of the pleats 8, 9, sheets 2, 3 and the panel 4 are folded along two fold lines 10, 11 extending in the transverse direction so as to present a Z-shaped cross-section.

These pleats 8, 9 extend outward on the outer surface of the base sheet 3 wherein the pleat 8 is collapsed onto the end flap 6 in the front waist region 20 and the pleat 9 is collapsed onto the end flap 6 in the rear waist region 22. The pleats 8, 9 respectively have transversely opposite end zones 8a, 9a joined to the side flaps 7 by means of hot melt adhesive so that these end zones 8a, 9a may be retained in the collapsed state.

The panel 4 is entirely covered with and joined to tissue paper (not shown) and then joined to inner surfaces of the topsheet 2 and the base sheet 3 with the tissue paper therebetween.

The leak-barrier cuffs 5 are provided on the side flaps 7 and extend in the longitudinal direction. The cuffs 5 respectively have fixed edge regions 5a extending immediately outside the respective side edges 4b of the panel 4, free edge regions 5b normally biased to rise on the topsheet 2 and longitudinally opposite end regions 5c collapsed inward transversely of the diaper 1 and fixed in such collapsed state. The leak-barrier cuffs 5 further have the outermost lateral regions 5d extending from the respective fixed edge regions 5a outward transversely of the diaper 1. Elastic members 13 extending in the longitudinal direction are attached under extension to the respective free edge regions 5b so that the free edge regions 5b partially cover the respective elastic members 13.

The end flaps 6 respectively have ribbon-like elastic members 14 operatively associated with a waist-hole attached under extension thereto so as to extend in the transverse direction. In the crotch region 21, the side flaps 7 respectively have a plurality of elastic members 15 operatively associated with a pair of leg-holes attached thereto so as to extend in the longitudinal direction.

In the end flaps 6, longitudinal end regions 2a of the topsheet 2 as well as longitudinal end regions 3a of the base sheet 3 extend longitudinally outward beyond the longitudinal ends 4a of the panel 4 and these end regions 2a, 3a are overlaid and joined together, as seen in FIG. 2. The elastic members 14 operatively associated with the waist-hole are disposed between the longitudinal end regions 2a of the topsheet 2 and the longitudinal end regions 3a of the base sheet 3 and joined to these end portions 2a, 3a. Both of the fixed end regions 5c of the respective leak-barrier cuffs 5 are joined to the longitudinally opposite end regions 2a of the topsheet 2, respectively.

In the side flaps 7, side edge regions 2b of the topsheet 2 extend transversely outward slightly beyond the side edges 4b of the panel 4 and side edge regions 3b of the base sheet 3 as well as side edge regions 5d of the leak-barrier cuffs 5 further extend transversely outward beyond the side edge regions 2b of the topsheet 2. The side edge regions 2b are disposed between the side edge regions 3b and the side edge regions 5d and joined to these side edge regions 3b, 5b. The side edge regions 3b and the side edge regions 5d extending transversely outward beyond the side edge regions are overlaid and joined to each other. The elastic members 15 operatively associated with the leg-holes are disposed between the side edge regions 3b of the base sheet 3 and the side edge regions 5d of the leak-barrier cuffs 5 and joined to these side edge regions 3b, 5b. The fixed edge regions 5a of the leak-barrier cuffs 5 are joined to the side edge regions 2b of the topsheet 2.

In the rear waist region 22, the side flaps 7 are respectively provided with tape fasteners 16 extending inward in the transverse direction. The tape fasteners 16 respectively have proximal end regions disposed between the side edge regions 3b of the base sheet 3 and the side edge regions 5d of the leak-barrier cuffs 5 and joined to these side edge regions 3b, 5d. The tape fasteners 16 respectively have free end regions coated with pressure-sensitive adhesive (not shown). In the front waist region 20, the base sheet 3 is provided on its outer surface with a rectangular target tape strip 17 made of a plastic film. The target tape strip 17 serves as an anchoring zone for the tape fasteners 16.

Figure 5:
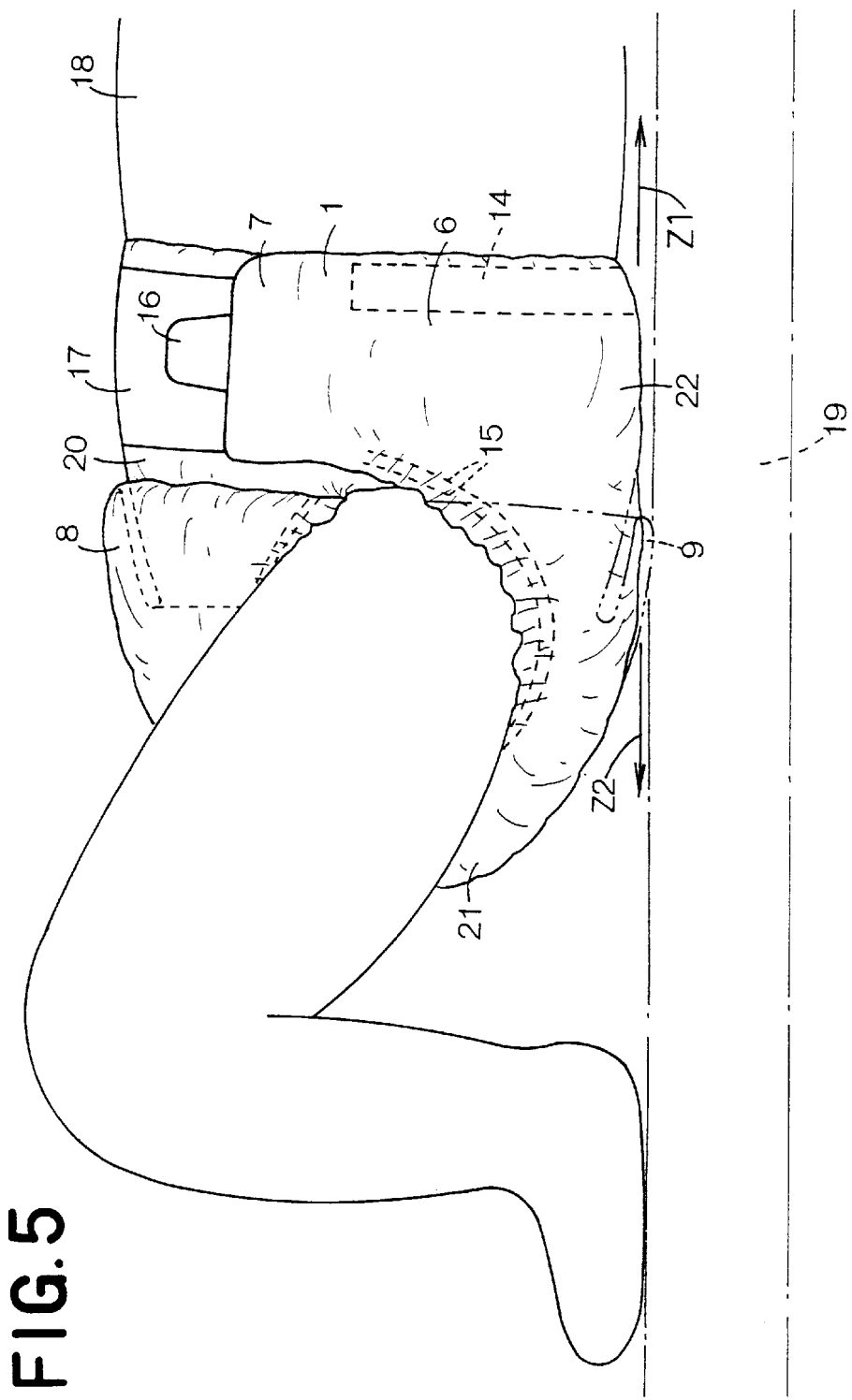
FIG. 5 is a side view of the diaper as being worn with its front and rear waist regions connected to each other.

FIG. 5 is a side view showing the diaper 1 as being worn with its front and rear waist regions 20, 22 connected to each other and FIG. 6 is also a side view showing the diaper 1 as being worn with its front and rear waist regions 20, 22 connected to each other. Both FIG. 5 and FIG. 6 illustrate a wearer 18 of the diaper 1 lying with his or her face up on bedding 19 indicated by single-dotted chain line. To wear the diaper 1, the side flaps 6 in the rear waist region 22 may be placed upon the outer side of the front waist region 20, then the free end regions of the respective tape fasteners 16 may be anchored on the target tape strip 17 by means of the pressure-sensitive adhesive to connect the front waist region 20 with the rear waist region 22. Upon connection of the front and rear waist regions 20, 22, the waist-hole and the pair of leg-holes are defined in the diaper 1.

Movement of the wearer 18 in a direction indicated by an arrow Z1 in FIG. 5 causes the rear waist region 22 of the diaper 1 to slip downward along the waist of the wearer 18 by a frictional force generated between the diaper 1 and the bedding 19. However, prior to the slippage of the rear waist region 22, the pleat 9 indicated by two-dotted chain line in FIG. 5 is unfolded in a direction indicated by an arrow Z2 so as to prevent the rear waist region 22 from slipping downward.

Movement of the wearer 18 in a direction indicated by an arrow Z3 in FIG. 6 causes the rear waist region 22 to slip upward and consequently drags the front waist region 20 downward along the waist of the wearer 18. However, prior to the movement of the front waist region 20, the pleat 8 indicated by two-dotted chain line in FIG. 6 is unfolded in a direction indicated by an arrow Z4 serving to prevent the front waist region 20 from slipping downward.

While the pleats 8, 9 are illustrated to be formed in the crotch region's front zone 21a and the crotch region's rear zone 21b, respectively, it is possible to form such pleat 8 or 9 in one of the crotch region's front zone 21a and rear zone 21b.

As will be apparent from FIG. 2, these pleats 8, 9 are normally collapsed onto the end flaps 6, respectively. The front and rear waist regions 20, 22 lie above the crotch region's front and rear zones 21a, 21b as viewed in FIG. 2 so as to define a level difference between the front waist regions 20 and the crotch region's front zone 21a as well as between the rear waist region 22 and the crotch region's rear zone 21b.

Excretion discharged onto the crotch region 21 must flow over level differences to spread into the front and rear waist regions 20, 22. Specifically, the diaper 1 according to this invention effectively prevents the excretion discharged onto the crotch region 21 from further spreading into the front and rear waist regions 20, 22.

With this diaper 1, the free edge regions 5b of the leak-barrier cuffs 5 uprise on the topsheet 2 as the diaper 1 curves in the longitudinal direction with the topsheet 2 inside. The side edge regions 5b thus uprising on the topsheet 2 form barriers against body wastes and reliably prevent such body wastes from leaking beyond the respective side flaps 7.

The topsheet 2 may be formed of a hydrophilic fibrous nonwoven fabric or finely porous plastic film. The base sheet 3 may be formed from a hydrophobic fibrous nonwoven fabric, a liquid-impervious plastic film, a two-layered hydrophobic nonwoven fabric, or a composite sheet consisting of a hydrophobic fibrous nonwoven fabric laminated with a plastic film. The leak-barrier cuffs 5 may be formed using a hydrophobic fibrous nonwoven fabric.

It is also possible to employ for the base sheet 3 as well as the leak-barrier cuffs 5 a composite nonwoven fabric composed of fibrous nonwoven fabric made by melt blown process having a high water-resistant property sandwiched by fibrous nonwoven fabric having high strength and flexibility made by spun bond process.

The nonwoven fabric may be selected from a group of materials of those obtained by spun lacing, needle punching, melt blowing, thermal bonding, spun bonding, chemical bonding and air-through processes. The component fibers of such nonwoven fabric may be selected from a group of materials of polyolefine-, polyester- and polyamide-fiber, and core-sheath type conjugated fiber or side-by-side type conjugated fiber of polyethylene/polypropylene or polyethylene/polyester.

The panel 4 comprises a mixture of fluff pulp and super-absorptive polymer particles or a mixture of fluff pulp, super-absorptive polymer particles and thermoplastic synthetic resin fiber compressed together to a desired thickness. The polymer may be selected from a group of materials of starch-based polymer, cellulose-based polymer and synthetic polymer.

In the diaper 1, the presence of the topsheet 2 is not essential so far as the base sheet 3 is provided with the liquid-absorbent panel 4 attached thereto. In this case, the panel 4 preferably comprises fibrous web with appropriate compressive restoring elasticity, which contains the super-absorptive polymer particles dispersed and held in fiber-interstices thereof and which has been compressed to a desired thickness to give a shape stability. The component fibers of such fibrous web may be selected from a group of materials of polyolefine-based fibers such as polypropylene or polyethylene, polyester-based fibers such as polyethylene terephthalate, polyamide-based fibers such as nylon 66 or nylon 6, acryl-based fibers, and cellulose-based fiber such as pulp, rayon or acetate.

Bonding between the topsheet 2 and the base sheet 3, fixing of the leak-barrier cuffs 5, joining of the panel 4, and attachment of the respective elastic members 12, 13, 14 may be achieved using hot melt adhesive or heat welding technique such as heat-sealing or supersonic-sealing.

The disposable diaper according to this invention comprises pleats extending in the transverse direction to provide the diaper with an easiness with which the diaper is stretchable in the longitudinal direction. Even if the diaper frictionally moves on the bedding or the floor and the frictional force intends to slip the front and/or rear waist regions of the diaper downward, the pleats are unfolded in the longitudinal direction prior to such slippage and thereby prevent the front and/or rear waist regions from actually slipping down. The diaper according to this invention is adapted to prevent such slippage in this way and thereby maintains the inner surface of the diaper in contact with the wearer's skin during use of the diaper. Consequently, the liquid-absorbent panel can immediately absorb and retain the body wastes.

According to the embodiment in which the pleats are normally collapsed onto the end flaps, the level differences are defined between the front waist region and the crotch region's front zone as well as between the rear waist region and the crotch region's rear zone. These level differences advantageously serve as barriers against transfer of the body wastes from the crotch region to the front and rear waist regions, preventing the body wastes from spreading further into the front and rear waist regions.

What is claimed is:

1. A disposable diaper comprising:
   a front waist region;
   a rear waist region;
   a crotch region extending between the front waist region and the rear waist region:
   a substantially liquid-impervious base sheet;
   a liquid-absorbent panel placed onto said substantially liquid-impervious base sheet;
   a pair of end flaps extending in a transverse direction immediately outside longitudinal opposite ends of said liquid-absorbent panel;
   a pair of side flaps extending in a longitudinal direction immediately outside transversely opposite side edges of said liquid-absorbent panel;
   at least one pleat defined by folding said substantially liquid-impervious base sheet and said liquid-absorbent panel together, said at least one pleat extending in the traverse direction across at least one of a front zone of said crotch region adjacent to said front waist region and a rear zone of said crotch region adjacent to said rear waist region, said pleat having transversely opposite end regions thereof joined to said pair of side flaps.

2. The disposable diaper according to claim 1, wherein said at least one pleat extends outward from an outer surface of said substantially liquid-impervious base sheet and is normally collapsed onto said pair of end flaps.

3. A disposable diaper comprising:
   a front waist region;
   a rear waist region;
   a crotch region extending between the front waist region and the rear waist region;
   a substantially liquid-impervious base sheet;
   a liquid-absorbent panel placed onto said substantially liquid-impervious base sheet;
   a pair of end flaps extending in a transverse direction immediately outside longitudinal opposite ends of said liquid-absorbent panel;
   a pair of Bide flaps extending in a longitudinal direction immediately outside transversely opposite side edges of said liquid-absorbent panel;
   at least one pleat defined by folding said substantially liquid-impervious base sheet and said liquid-absorbent panel together in a z-fold configuration, said at least one pleat extending in the transverse direction across at least one of a front zone of said crotch region adjacent to said front waist region and a rear zone of said crotch region adjacent to said rear waist region, said pleat having transversely opposite end regions thereof joined to said pair of side flaps.

4. The disposable diaper according to claim 3, wherein said at Least one pleat extends outward from an outer surface of said substantially liquid-impervious base sheet and is normally collapsed onto said pair of end flaps.

5. A disposable diaper comprising:
   a front waist region;
   a rear waist region;
   a crotch region extending between the front waist region and the rear waist region;
   a topsheet;
   a substantially liquid-impervious base sheet;
   a liquid-absorbent panel position between said topsheet and said substantially liquid- impervious base sheet;
   a pair of end flaps extending in a transverse direction immediately outside longitudinal opposite ends of said liquid-absorbent panel;
   a pair of side flaps extending in a longitudinal direction immediately outside transversely opposite side edges of said liquid-absorbent panel;
   at least one pleat defined by folding each of said substantially liquid-impervious base sheet, said topsheet, and said liquid-absorbent panel together, said at least one pleat extending in the transverse direction across at least one of a front zone of said crotch region adjacent to said front waist region and a rear zone of said crotch region adjacent to said rear waist region, said pleat having transversely opposite end regions thereof joined to said pair of side flaps.

6. The disposable diaper according to claim 5, wherein said at least one pleat extends outward from an outer surface of said substantially liquid-impervious base sheet and is normally collapsed onto said pair of end flaps.

* * * * *